United States Patent
Dintenfass et al.

(10) Patent No.: US 10,153,056 B2
(45) Date of Patent: Dec. 11, 2018

(54) SYSTEM FOR A GEOGRAPHIC LOCATION BASED SHARING REQUEST NETWORK

(71) Applicant: BANK OF AMERICA CORPORATION, Charlotte, NC (US)

(72) Inventors: Katherine Dintenfass, Lincoln, RI (US); Vasudevan Nagalingam, Wayland, MA (US)

(73) Assignee: BANK OF AMERICA CORPORATION, Charlotte, NC (US)

( * ) Notice: Subject to any disclaimer, the term of this patent is extended or adjusted under 35 U.S.C. 154(b) by 261 days.

(21) Appl. No.: 15/223,667

(22) Filed: Jul. 29, 2016

(65) Prior Publication Data

US 2017/0323398 A1    Nov. 9, 2017

Related U.S. Application Data (60) Provisional application No. 62/333,723, filed on May 9, 2016.

(51) Int. Cl.
*G06F 17/30* (2006.01)
*G16H 40/63* (2018.01)
(Continued)

(52) U.S. Cl.
CPC ......... *G16H 40/63* (2018.01); *G06F 17/3087* (2013.01); *G06F 17/30165* (2013.01);
(Continued)

(58) Field of Classification Search
CPC .............................................. G06F 17/30165
(Continued)

(56) References Cited

U.S. PATENT DOCUMENTS

| 5,920,848 A | 7/1999 | Schutzer et al. |
| 5,987,433 A | 11/1999 | Crapo |

(Continued)

FOREIGN PATENT DOCUMENTS

| WO | 0118728 A2 | 3/2001 |
| WO | 2003100645 A1 | 12/2003 |

(Continued)

OTHER PUBLICATIONS http://budgettracker.com retrieved on Jun. 9, 2009.
(Continued)

*Primary Examiner* — Chelcie L Daye
(74) *Attorney, Agent, or Firm* — Michael A. Springs; Moore & Van Allen PLLC; Nicholas C. Russell (57) ABSTRACT

Embodiments of the invention are directed to a system, method, or computer program product for building a geographic location based sharing request network. The invention generates and builds a sharing request network based on user geographic locations for efficiently and conveniently matching and connecting users to one another and third party systems. In this way, the sharing request network system may identify social events, volunteering opportunities, medical aid sharing, and transportation sharing for aging individuals. Furthermore, the system generates a knowledge sharing advice database, since aging individuals typically have professional or personal experiences. The user may be able to respond with answers or advice to questions posted by other users via the system. Additionally, the system may generate rewards based on the knowledge or advice provided in response to posted questions.

16 Claims, 4 Drawing Sheets

(51) Int. Cl.

| | | |
|---|---|---|
| *G06Q 40/06* | (2012.01) | |
| *G06Q 30/02* | (2012.01) | |
| *G06Q 30/06* | (2012.01) | |
| *H04L 29/08* | (2006.01) | |
| *G06Q 20/38* | (2012.01) | |
| *G06Q 20/40* | (2012.01) | |
| *G06Q 50/00* | (2012.01) | |
| *G06F 21/62* | (2013.01) | |
| *H04L 29/06* | (2006.01) | |
| *G06Q 10/10* | (2012.01) | |
| *G06F 19/00* | (2018.01) | |
| *G06Q 50/16* | (2012.01) | |

(52) U.S. Cl.
CPC .. *G06F 17/30241* (2013.01); *G06F 17/30554* (2013.01); *G06F 17/30699* (2013.01); *G06F 17/30867* (2013.01); *G06F 19/00* (2013.01); *G06F 21/6245* (2013.01); *G06Q 10/1057* (2013.01); *G06Q 20/3821* (2013.01); *G06Q 20/4014* (2013.01); *G06Q 30/0201* (2013.01); *G06Q 30/0226* (2013.01); *G06Q 30/0645* (2013.01); *G06Q 40/06* (2013.01); *G06Q 50/01* (2013.01); *H04L 63/08* (2013.01); *H04L 63/083* (2013.01); *H04L 67/10* (2013.01); *H04L 67/18* (2013.01); *H04L 67/20* (2013.01); *H04L 67/306* (2013.01); *G06Q 50/16* (2013.01)

(58) Field of Classification Search
USPC .................................. 707/722; 705/13
See application file for complete search history.

(56) References Cited

U.S. PATENT DOCUMENTS

| | | |
|---|---|---|
| 6,014,632 A | 1/2000 | Gamble et al. |
| 6,684,190 B1 | 1/2004 | Powers et al. |
| 6,985,880 B1 | 1/2006 | Hodgdon et al. |
| 7,062,572 B1 | 6/2006 | Hampton |
| 7,069,308 B2 | 6/2006 | Abrams |
| 7,174,313 B1 | 2/2007 | Martinez |
| 7,216,099 B2 | 5/2007 | Chen et al. |
| 7,295,832 B2 | 11/2007 | Hewel |
| 7,299,007 B2 | 11/2007 | Eskin |
| 7,475,032 B1 | 1/2009 | Patnode et al. |
| 7,634,436 B1 | 12/2009 | Wagner |
| 7,657,655 B2 | 2/2010 | Hampton |
| 7,660,744 B2 | 2/2010 | Philippe et al. |
| 7,668,764 B2 | 2/2010 | Wilson |
| 7,725,387 B1 | 5/2010 | Fitch et al. |
| 7,822,671 B1 | 10/2010 | Oros |
| 7,840,463 B1 | 11/2010 | Davis |
| 7,840,470 B2 | 11/2010 | Robinson |
| 7,865,419 B2 | 1/2011 | Rojeck et al. |
| 7,895,102 B1 | 2/2011 | Wilks et al. |
| 7,945,458 B1 | 5/2011 | Jackson |
| 7,949,592 B1 | 5/2011 | Oros |
| 8,050,995 B1 | 11/2011 | Landry et al. |
| 8,069,103 B1 | 11/2011 | Davis |
| 8,332,297 B1 | 12/2012 | Claus et al. |
| 8,429,091 B2 | 4/2013 | Buyukkokten et al. |
| 8,458,044 B2 | 6/2013 | Blair et al. |
| 8,484,109 B1 | 7/2013 | Deurmier et al. |
| 8,504,435 B2 | 8/2013 | Charles |
| 8,527,382 B2 | 9/2013 | McDonough et al. |
| 8,551,186 B1 | 10/2013 | Strand |
| 8,567,672 B2 | 10/2013 | Mesaros |
| 8,590,785 B1 | 11/2013 | Mesaros |
| 8,606,630 B2 | 12/2013 | Fordyce, III et al. |
| 8,635,226 B2 | 1/2014 | Chang et al. |
| 8,639,567 B2 | 1/2014 | Winters |
| 8,639,622 B1 | 1/2014 | Moore et al. |
| 8,639,650 B1 | 1/2014 | Gill |
| 8,676,687 B2 | 3/2014 | McDonough et al. |
| 8,688,556 B2 | 4/2014 | Greene et al. |
| 8,719,132 B1 | 5/2014 | Diggdon et al. |
| 8,782,136 B1 | 7/2014 | Ho et al. |
| 9,002,272 B2 | 4/2015 | Friedlaender |
| 9,064,284 B1 | 6/2015 | Janiszeski et al. |
| 9,077,677 B2 | 7/2015 | Mackin |
| 2002/0133706 A1 | 9/2002 | Khanna et al. |
| 2002/0198801 A1 | 12/2002 | Dixon et al. |
| 2003/0028466 A1 | 2/2003 | Jenson et al. |
| 2003/0105692 A1 | 6/2003 | Gilbert et al. |
| 2003/0233278 A1 | 12/2003 | Marshall |
| 2004/0111370 A1 | 6/2004 | Saylors et al. |
| 2004/0177036 A1 | 9/2004 | Nutahara et al. |
| 2005/0080725 A1 | 4/2005 | Pick |
| 2005/0096973 A1 | 5/2005 | Heyse et al. |
| 2005/0144108 A1 | 6/2005 | Loeper |
| 2005/0149436 A1 | 7/2005 | Elterich |
| 2005/0198305 A1 | 9/2005 | Pezaris et al. |
| 2006/0031150 A1 | 2/2006 | Senturk et al. |
| 2006/0224435 A1 | 10/2006 | Male et al. |
| 2007/0099166 A1 | 5/2007 | Moesges et al. |
| 2007/0192224 A1 | 8/2007 | Quayle et al. |
| 2007/0250427 A1 | 10/2007 | Robinson |
| 2007/0282699 A1 | 12/2007 | Kumar et al. |
| 2007/0288399 A1 | 12/2007 | Reynolds |
| 2008/0040276 A1 | 2/2008 | Hammad et al. |
| 2008/0189189 A1 | 8/2008 | Morgenstern |
| 2008/0215501 A1 | 9/2008 | Rojeck et al. |
| 2008/0217397 A1 | 9/2008 | Degliantoni et al. |
| 2008/0270304 A1 | 10/2008 | Brown |
| 2009/0024540 A1 | 1/2009 | Ryder |
| 2009/0030819 A1 | 1/2009 | VanLeeuwen |
| 2009/0146947 A1 | 6/2009 | Ng |
| 2009/0204528 A1 | 8/2009 | Moses |
| 2009/0307314 A1 | 12/2009 | Smith et al. |
| 2009/0326339 A1 | 12/2009 | Horvitz |
| 2009/0327308 A1 | 12/2009 | Carter et al. |
| 2010/0030686 A1 | 2/2010 | Lee et al. |
| 2010/0057574 A1 | 3/2010 | Banerjee et al. |
| 2010/0094740 A1 | 4/2010 | Richter |
| 2010/0100469 A1 | 4/2010 | Buchanan et al. |
| 2010/0205112 A1 | 8/2010 | Reynolds et al. |
| 2010/0241559 A1 | 9/2010 | O'Connor et al. |
| 2010/0268629 A1 | 10/2010 | Ross et al. |
| 2010/0274610 A1 | 10/2010 | Andersen et al. |
| 2010/0306126 A1 | 12/2010 | Moran et al. |
| 2011/0055008 A1 | 3/2011 | Feuerstein et al. |
| 2011/0106631 A1 | 5/2011 | Lieberman et al. |
| 2011/0106682 A1 | 5/2011 | Rojeck et al. |
| 2011/0106691 A1 | 5/2011 | Clark et al. |
| 2011/0131089 A1 | 6/2011 | Walker et al. |
| 2011/0166978 A1 | 7/2011 | Mastrogiovanni |
| 2011/0191173 A1 | 8/2011 | Blackhurst et al. |
| 2011/0213665 A1 | 9/2011 | Joa et al. |
| 2011/0231305 A1 | 9/2011 | Winters |
| 2011/0246279 A1 | 10/2011 | Joa et al. |
| 2011/0246306 A1* | 10/2011 | Blackhurst ............ G06Q 30/02 705/14.58 |
| 2011/0276410 A1 | 11/2011 | Hjelm et al. |
| 2012/0047022 A1 | 2/2012 | Shamim et al. |
| 2012/0123857 A1 | 5/2012 | Surve et al. |
| 2012/0214571 A1 | 8/2012 | Oakes et al. |
| 2012/0265819 A1 | 10/2012 | McGann et al. |
| 2012/0284127 A1 | 11/2012 | Heiser, II et al. |
| 2013/0006756 A1 | 1/2013 | Heo |
| 2013/0046645 A1 | 2/2013 | Grigg et al. |
| 2013/0073388 A1 | 3/2013 | Heath |
| 2013/0073546 A1 | 3/2013 | Yan et al. |
| 2013/0096996 A1 | 4/2013 | Tabor et al. |
| 2013/0150139 A1 | 6/2013 | Oakes |
| 2013/0179254 A1 | 7/2013 | Joa et al. |
| 2013/0246147 A1 | 9/2013 | Chen et al. |
| 2013/0325748 A1 | 12/2013 | Suri et al. |
| 2014/0032293 A1 | 1/2014 | Donlan et al. |
| 2014/0046748 A1 | 2/2014 | Nagarajan et al. |
| 2014/0114882 A1 | 4/2014 | Thoma |
| 2014/0136323 A1 | 5/2014 | Zhang et al. |

(56) References Cited

U.S. PATENT DOCUMENTS

| | | | |
|---|---|---|---|
| 2014/0230019 A1 | 8/2014 | Civelli et al. | |
| 2014/0282877 A1 | 9/2014 | Mahaffey et al. | |
| 2014/0380445 A1 | 12/2014 | Tunnell et al. | |
| 2015/0019523 A1 | 1/2015 | Lior et al. | |
| 2015/0040203 A1 | 2/2015 | Qian | |
| 2015/0178844 A1 | 6/2015 | Ross et al. | |
| 2015/0228000 A1* | 8/2015 | Bijor | G06Q 30/0613 705/13 |
| 2015/0363562 A1 | 12/2015 | Hallwachs | |
| 2015/0363563 A1 | 12/2015 | Hallwachs | |
| 2016/0012249 A1 | 1/2016 | Keppler | |
| 2016/0027079 A1* | 1/2016 | Schoeffler | G06Q 30/0609 705/325 |
| 2016/0171574 A1* | 6/2016 | Paulucci | G07B 15/02 705/13 |
| 2016/0275615 A1 | 9/2016 | Dintenfass et al. | |
| 2017/0193404 A1* | 7/2017 | Yoo | G06Q 10/02 |

FOREIGN PATENT DOCUMENTS

| | | |
|---|---|---|
| WO | 2005059799 A2 | 6/2005 |
| WO | 2010045058 A1 | 4/2010 |
| WO | 2010045059 A1 | 4/2010 |
| WO | 2013008128 A1 | 1/2013 |
| WO | 2014104436 A1 | 7/2014 |
| WO | 2015034937 A1 | 3/2015 |
| WO | 2015192121 A1 | 12/2015 |

OTHER PUBLICATIONS http://buxfer.com retrieved on Jun. 9, 2009.
http://personal.fidelity.com/planning/retirement/retiree/content/imademo.shtml# retrieved on Sep. 24, 2008.
http://www.mint.com/features/auto/ retrieved on Jul. 99, 2009.
http://www.mvelopes.com/overview retrieved on Jun. 9, 2009.
http://www.nytimes.com/2008/12/07/weekinreview/07dash.html?_=3&ref=weekinreview retrieved on Mar. 27, 2009.
http://www.pncvirtualwallet.com/main.html retrieved on Nov. 24, 2008.
http://yodlee.com/solutions_pfm_ypf.shtml retrieved on Jun. 9, 2009.
http:/www.digitalreceipts.com retrieved on Jun. 11, 2009.
https://www.budgetpulse.com retrieved on Jun. 9, 2009.
https://www.pearbudget.com retrieved on Jun. 9, 2009.
International Search Report for International Application PCT/US2010/35192 dated Jul. 8, 2010.
International Search Report for International Application PCT/US2010/30872 dated Jun. 7, 2010.
International Search Report for International Application PCT/US2010/02162 dated May 2, 2011.

* cited by examiner

SYSTEM FOR A GEOGRAPHIC LOCATION BASED SHARING REQUEST NETWORK

CROSS-REFERENCE TO RELATED APPLICATIONS

This application is a continuation of U.S. Provisional Patent Application Ser. No. 62/333,723, filed May 9, 2016, entitled "System for Optimizing Resource Usage," the entirety of which is incorporated herein by reference.

BACKGROUND

Aging individuals often desire to connect with nearby, like-minded individuals for group or community activities. Additionally, these individuals may also require or desire transportation for errands, appointments, social gatherings, and the like. While systems and applications for making connections exist, there is a need for a unified system for connecting aging individuals in order to provided needed support and allow them to efficiently and conveniently fulfill various requests through sharing of resources and time.

BRIEF SUMMARY

The following presents a simplified summary of one or more embodiments of the invention in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

Embodiments of the present invention address these and/or other needs by providing an innovative system, method, and computer program product for a geographic location based sharing request network allowing users to request and share resources with one another.

In some embodiments, the system generates and builds a sharing request network based on user geographic locations for matching and connecting of similarly situated users. In this way, the system may identify social events, volunteering opportunities, and the like for aging individuals. The system may further include medical aid sharing and the like for the aging individuals. Furthermore, in some embodiments, the system may provide a ride sharing component for traveling. Furthermore, the system generates a knowledge sharing advice database. Since aging individuals typically have professional or personal experiences, the user may be able to provide advice via the system and the system may generate rewards based on knowledge or advice provided.

Embodiments of the invention related to systems, methods, and computer program products for building a sharing request network, the system comprising: a memory device with computer-readable program code stored thereon; a communication device; a processing device operatively coupled to the memory device and the communication device, wherein the processing device is configured to execute the computer-readable program code to: receive authentication and acceptance from a user for entry into the sharing request network; generate a communication link with a user device for extraction of positioning data associated with the user device, wherein the user device is associated with the user; generate a user profile identifying user request events and a location of the user device from the positioning data; based on the user profile, match the user to one or more additional users and third party systems for event coordination, wherein the third party systems offer products or services; and trigger a communicable linkage between the user, the one or more additional users, and the third party systems for coordination of resource sharing, wherein matching user information is transmitted and presented to matched users over the communicable linkage.

In some embodiments of the invention, generating the user profile further comprises: transmitting a control signal to the user device causing the user device to display a data request via a graphical user interface; prompting the user for personal information and user preferences; generating a username and password associated with the user profile; linking one or more social media accounts associated with the user to the user profile; and extracting information from the personal information, the user preferences, and the one or more social media accounts to generate the user profile.

In some embodiments of the invention, prompting the user for personal information and user preferences further comprises: requesting access to one or more financial accounts associated with the user; and extracting personal information, financial account information, and transaction history from the one or more financial accounts to be used for at least partially generating the user profile.

In some embodiments of the invention, matching the user to one or more additional users and third party systems further comprises: determining the location of the user device based on extracted positioning data; determining one or more additional locations of one or more additional user devices associated with the one or more additional users based on additional positioning data extracted from the one or more additional user devices; and based on determining that the first location and the one or more additional locations are within a predetermined distance of each other, trigger a match between the user, the one or more additional users, and the third party systems.

In some embodiments of the invention, the third party systems for event coordination comprise systems for transportation coordination and sharing, wherein the positioning data associated with the user device is transmitted to the third party systems for determining the location of the user and coordinating transportation.

In some embodiments of the invention, the user profile is stored in a centralized database.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Having thus described embodiments of the invention in general terms, reference will now be made to the accompanying drawings, wherein:

DETAILED DESCRIPTION OF THE INVENTION

In some embodiments, the system initiates building the sharing request network. In some embodiments, a user is authorized into the system via a request. In this way, the user authorizes access into the sharing request network and distributive network built within. Once a request is initiated, the geographical location of the user may be determined. In this way, the system may retrieve geographical location information of the user base on a secure communication linkage with a device associated with the user. The device may include a mobile device with a cellular location signal, a global positioning device, a computer device, telephone device, or the like that is capable of transmitting a location of the user.

Once a user is authorized to the system, a user profile may be generated. The user profile may contain the geographic location data of the user, extracted data, and user inputted data. The extracted data may include information the system may have access to via linkage to network systems. In some embodiments, the system may have access to data associated with financial activity, financial history of the user. For example, the system may identify products the user has purchased, merchants the user has shopped, medical requirements of the user, and the like. With this information, the system may be able to identify patterns of user financial activity and trends associated with the same.

In some embodiments, the user may input data into the user profile. This data may be information about medical needs, social desires, volunteer requests, travel requirements, and/or information in the form of questions or aids onto the knowledge database. In some embodiments, the knowledge database comprises a question posting and answering application generated by the users. Based on the user profile, the system may identify one or more areas of expertise of the user. Since the users are typically advanced aged, the user typically will have knowledge of one or more areas, such as areas of employment, building, construction, business, financial, or the like. The system may identify the experience areas of the user on the sharing request network. As such, the system may direct questions posted onto the knowledge database to specific users with experience in that area.

The present invention improves upon the process of connecting individuals with similar interests and/or corresponding requests by matching users based at least partially on the geographical location of the users and their proximity to one another. Additionally, matches may be performed in substantially real-time by utilizing the storage of user profile data on a centralized database which reduces the processing time required by the system to retrieve stored information and match users. The system matches users which triggers the transmission of user information associated with the matched users to one another. The user devices associated with the matched users are commanded to display a graphical user interface which displays the user information associated with the other matched user.

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to elements throughout. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein.

Furthermore, as used herein the term "user device" may refer to any device that employs a processor and memory and can perform computing functions, such as a personal computer or a mobile device, wherein a mobile device is any mobile communication device, such as a cellular telecommunications device (i.e., a cell phone or mobile phone), personal digital assistant (PDA), a mobile Internet accessing device, or other mobile device. Other types of mobile devices may include portable digital assistants (PDAs), pagers, wearable devices, mobile televisions, gaming devices, laptop computers, cameras, video recorders, audio/video player, radio, GPS devices, or any combination of the aforementioned.

Figure 1:
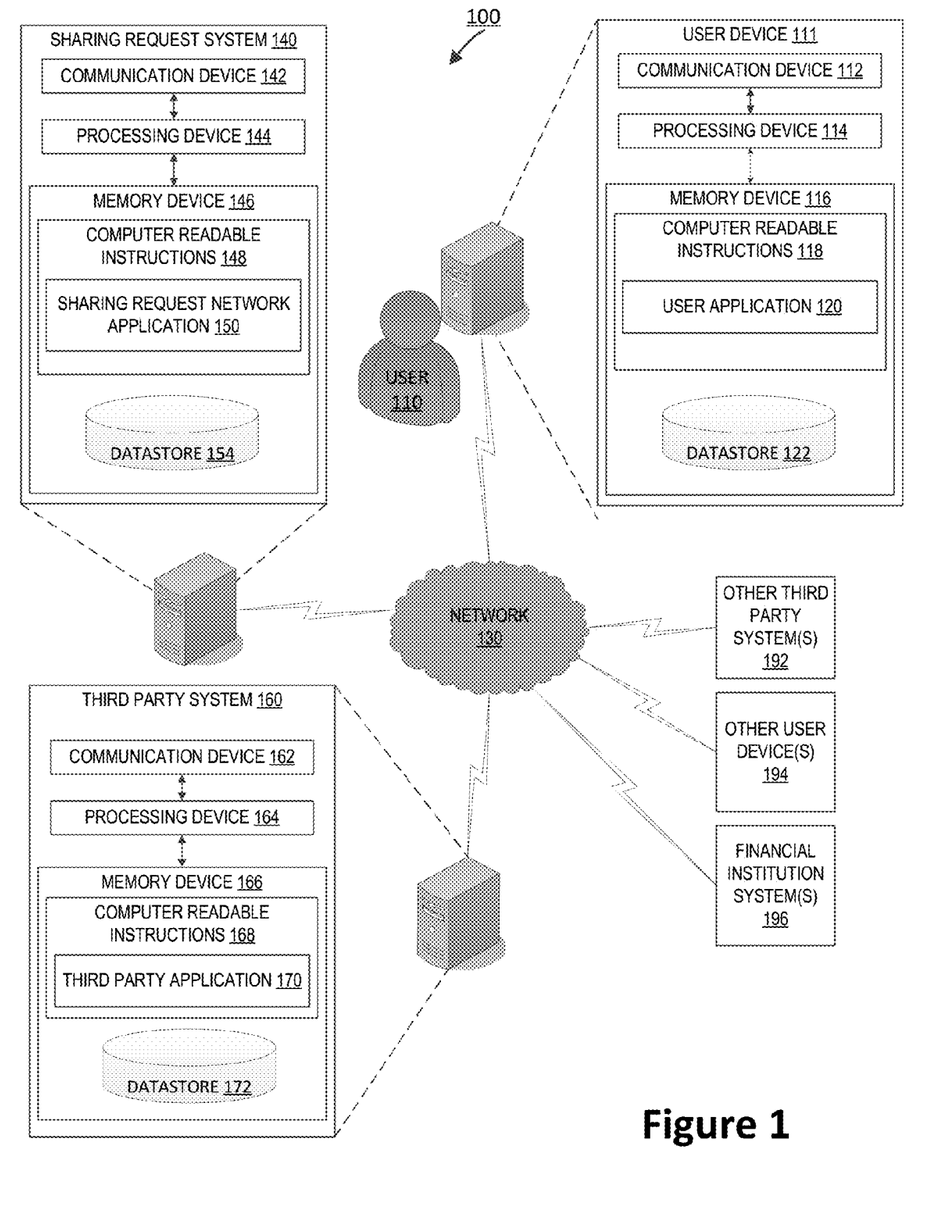
FIG. 1 provides a sharing request network system environment, in accordance with one embodiment of the present invention.

Referring to FIG. 1, the figure illustrates a sharing request system environment 100, in accordance with some embodiments of the invention. The environment 100 includes a user device 111 associated or used with authorization of a user 110 (e.g., a mobile application user, and the like), a third party system 160, and a sharing request system 140. In some embodiments, the third party system 160 corresponds to a third party provider of a service such as a transportation provider, medical care provider, and the like. In some embodiments, the financial institution system 1 The environment 100 further includes one or more other third party systems 192 (i.e., additional or other third party service providers), one or more other user devices 194 associated with other users within a network, and one or more financial institution systems 196 (e.g., a credit bureau, third party banks, and so forth).

The systems and devices communicate with one another over the network 130 and perform one or more of the various steps and/or methods according to embodiments of the disclosure discussed herein. The network 130 may include a local area network (LAN), a wide area network (WAN), and/or a global area network (GAN). The network 130 may provide for wireline, wireless, or a combination of wireline and wireless communication between devices in the network. In one embodiment, the network 130 includes the Internet.

The user device 111, the third party system 160, the financial institution system 196 and the sharing request system 140 each includes a computer system, server, multiple computer systems and/or servers or the like. The sharing request system 140, in the embodiments shown has a communication device 142 communicably coupled with a processing device 144, which is also communicably coupled with a memory device 146. The processing device 144 is configured to control the communication device 142 such that the sharing request system 140 communicates across the network 130 with one or more other systems. The processing device 144 is also configured to access the memory device 146 in order to read the computer readable instructions 148, which in some embodiments includes a sharing request network application 150. The sharing request network application 150 allows for the sharing request system 140 to communicate to the various other systems and devices within the environment 100. The functions of the sharing request network application 150 are further described in detail below. The memory device 146 also includes a datastore 154 or database for storing pieces of data that can be accessed by the processing device 144.

As used herein, a "processing device," generally refers to a device or combination of devices having circuitry used for implementing the communication and/or logic functions of a particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device 114, 144, or 164 may further include functionality to operate one or more software programs based on computer-executable program code thereof, which may be stored in a memory. As the phrase is used herein, a processing device 114, 144, or 164 may be "configured to" perform a certain function in a variety of ways, including, for example, by having one or more general-purpose circuits perform the function by executing particular computer-executable program code embodied in computer-readable medium, and/or by having one or more application-specific circuits perform the function.

Furthermore, as used herein, a "memory device" generally refers to a device or combination of devices that store one or more forms of computer-readable media and/or computer-executable program code/instructions. Computer-readable media is defined in greater detail below. For example, in one embodiment, the memory device 146 includes any computer memory that provides an actual or virtual space to temporarily or permanently store data and/or commands provided to the processing device 144 when it carries out its functions described herein.

The user device 111 includes a communication device 112 communicably coupled with a processing device 114, which is also communicably coupled with a memory device 116. In some embodiments, the communication device 112 may also comprise a GPS transceiver capable of determining a geographic location associated with the user device 111. The processing device 114 is configured to control the communication device 112 such that the user device 111 communicates across the network 130 with one or more other systems. The processing device 114 is also configured to access the memory device 116 in order to read the computer readable instructions 118, which in some embodiments includes a user application 120. The user application 120 allows for communication of the user device 111 with the other systems and devices within the environment 100 such as the sharing request system 140, third party system 160, third party system 192, and other user devices 194. The user application 120 allows the user 111 to input information requested by the sharing request system 140 and communicate with other users and third parties. The memory device 116 also includes a datastore 122 or database for storing pieces of data that can be accessed by the processing device 114.

The third party system 160 includes a communication device 162 communicably coupled with a processing device 164, which is also communicably coupled with a memory device 166. The processing device 164 is configured to control the communication device 162 such that the third party system 160 communicates across the network 130 with one or more other systems. The processing device 164 is also configured to access the memory device 166 in order to read the computer readable instructions 168, which in some embodiments includes a third party application. The third party application allows for communication with the other systems and devices within the environment 100 such as the user device 111, the sharing request system 140, and other user devices 194 in order to coordinate providing requested products or services to the users. The memory device 166 also includes a datastore 172 or database for storing pieces of data that can be accessed by the processing device 164.

The financial institution system 196 possesses a similar design to that of the other systems, wherein the financial institution system 196 possesses a financial institution application (not shown) which allows for communication with the other systems and devices within the environment 100 such as the sharing request system 140 and the user device 111 in order to allow and provide access to account information associated with the user 111 to the sharing request system 140.

The user application 120, the sharing request network application 150, and the third party application 170 are for instructing the processing devices 114, 144 and 164 respectively to perform various steps of the methods discussed herein, and/or other steps and/or similar steps. In various embodiments, one or more of the user application 120, the sharing request network application 150, and the third party application 170 are included in the computer readable instructions stored in a memory device of one or more systems or devices other than the third party system 160, sharing request system 140, and the user device 111. For example, in some embodiments, the user application 120 is stored and configured for being accessed by a processing device of one or more third party systems 192 connected to the network 130. In various embodiments, the user application 120, the sharing request network application 150, and the third party application 170 are stored and executed by different systems/devices. In some embodiments, the user application 120, the sharing request network application 150, and the third party application 170 stored and executed by different systems may be similar and may be configured to communicate with one another, and in some embodiments, the user application 120, the sharing request network application 150, and the third party application 170 may be considered to be working together as a singular application despite being stored and executed on different systems.

In various embodiments, one of the systems discussed above, such as the sharing request system 140, is more than one system and the various components of the system are not collocated, and in various embodiments, there are multiple components performing the functions indicated herein as a single device. For example, in one embodiment, multiple processing devices perform the functions of the processing device 144 of the sharing request system 140 described herein.

In various embodiments, the sharing request system 140, the third party system 160, the financial institution system 196 and the user device 111 and/or other systems may perform all or part of a one or more method steps discussed above and/or other method steps in association with the method steps discussed above. Furthermore, some or all the systems/devices discussed here, in association with other systems or without association with other systems, in association with steps being performed manually or without steps being performed manually, may perform one or more of the steps of one or more of the method discussed herein, or other methods, processes or steps discussed herein or not discussed herein.

In some embodiments, the invention builds a sharing request network application 150. The application compiles user data, such as information about the user, the user's geographic location, user interests, user hobbies, needs, medical requirements, or the like. Typically, in some embodiments of the invention, the user is an aging individual at or near retirement.

In the embodiment illustrated in FIG. 1 and described throughout much of this specification, the sharing request network application 150 may request and receive information from users including geographic location information, build a sharing request network using generated user profiles, and match users based on requests and collected user information.

In some embodiments of the invention, the sharing request network application 150 presents a user with data request for request network operations, for the sharing request network. As such, once a user has authenticated into the system, the application may push a request for input data for a user profile. The data request may be a request of input data to generate a user profile. The data requested may be for medical needs, social information, volunteer requests, travel requirements, and/or information in the form of questions or advice for the knowledge database.

Figure 4:
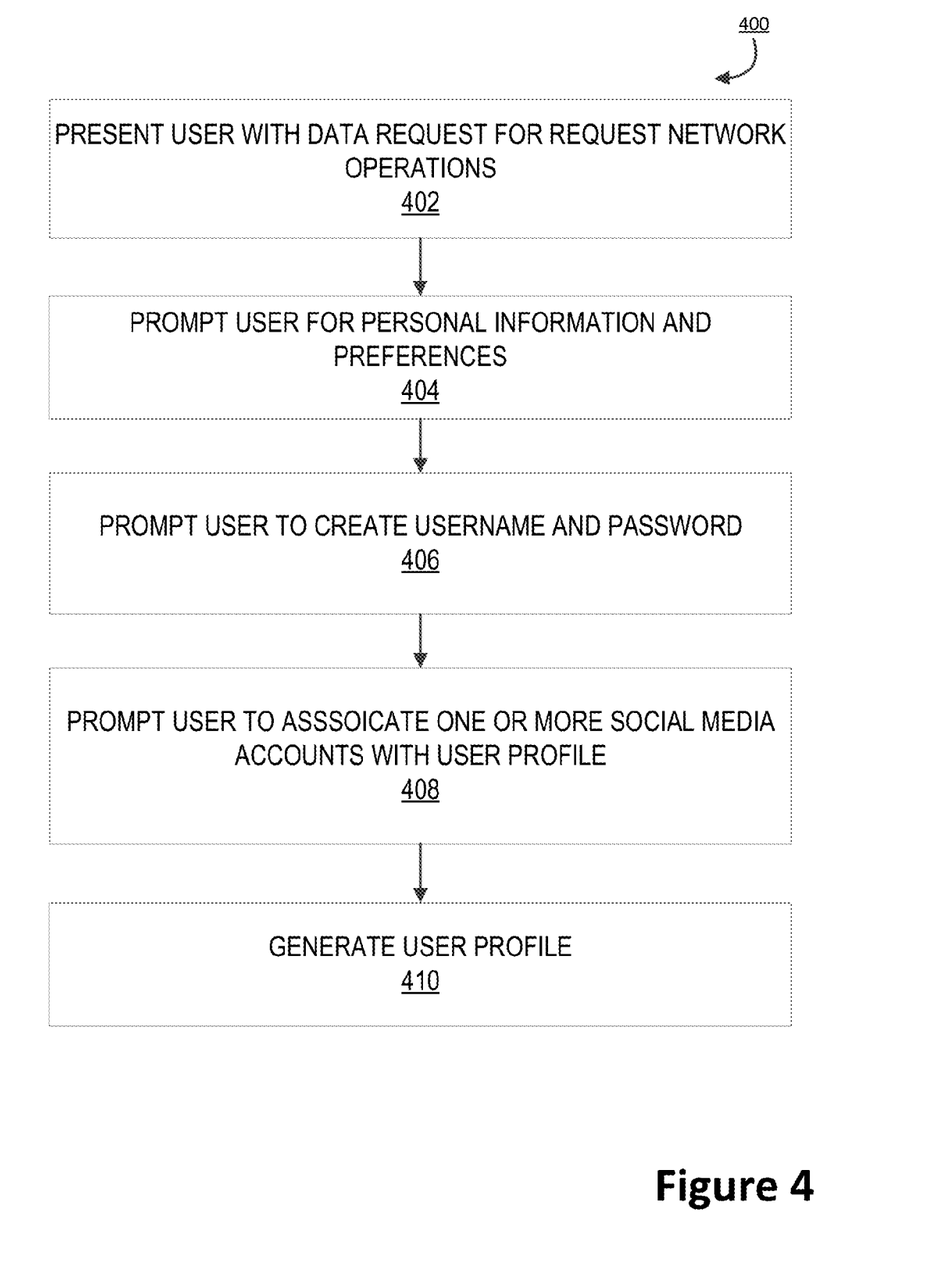
FIG. 4 provides a high level process flow for generating a user profile, in accordance with one embodiment of the present invention.

In some embodiments, the sharing request network application 150 next prompts the user for personal information and preferences to be associated with a user profile as illustrated in block 404. In some embodiments, the application prompts the user to provide personal information such as name, address, date of birth, phone number, email, medical records and the like. In some embodiments, personal information may include hobbies, interests, areas of expertise and the like. In some embodiments, the application prompts the user to provide or select preferences such as preferred events that the user might personally prefer over others. In some embodiments, the application prompts the user to provide or select preferences for potential matches such as a preferred age range, sex, or the like. The selection of preferences may additionally allow for better matching of like-minded users with similar preferences.

In some embodiments, the application generates communicable linkages with one or more financial institutions associated with a user. In this way, the application may retrieve financial information associated with the user such as transaction history, financial account information, and/or the like. In some embodiments, the application uses financial information to at least partially generate a user profile, wherein the financial information may be used to provide personal information and/or user preferences. In some embodiments, the application and sharing request network are maintained and operated by a financial institution. In other embodiments, the application and sharing request network are not maintained and operated by a financial institution.

In some embodiments, the sharing request network application 150 prompts a user to create a username and password to be associated with a user profile. The username and password provide identification of a user within the system while additionally providing a level of security for accessing the user profile within the application and system. In some embodiments, a user must first be authenticated by providing the username and password associated with a user profile before being allowed by the application to access the user profile and interact with other users within the sharing request network. In some embodiments, the application automatically creates a username for a user based off of the personal information and/or preferences provided by the user in the previous step.

In some embodiments, the sharing request network application 150 prompts the user to associate one or more social media accounts with the user profile. In some embodiments of the invention, the application may use information contained within the one or more social media accounts in order to populate the user profile with information related to the user. In some embodiments, the application provides social media accounts of a first user and a second user to one another upon the first user and the second user being matched.

In some embodiments, the user is prompted by the application to input data and/or personal information via the user device. Upon a user accessing the sharing request network, the application transmits a command signal to the user device causing the user device to display a graphical user interface containing fields for the user to input requested information or data.

In some embodiments, the sharing request network application 150 generates a user profile associated with a user. In some embodiments of the invention, the application compiles the data and information provided by a user into a user profile. In some embodiments, the application stores the user profile in the sharing request system 140. In other embodiments, the application stores the user profile in the user device 111. In some embodiments, the user profile is stored within the user application 120 on the user device 111.

In some embodiments, the sharing request network application 150 receives user data and a user profile associated with the sharing request network. The received data is categorized and analyzed. As previously discussed, this information is utilized to generate one or more user profiles which are compiled to build the sharing request network. This network may use the profiles to match various requests of the users with other users in the same geographic area for sharing of resources. Furthermore, based on the received information, the application may determine the experience of the user for the knowledge database. The application may determine one or more social, volunteering, medical, or travel needs or aids that the user may have.

In some embodiments, the sharing request network application 150 identifies the geographic location of the user. In this way, once a user is authorized into the system, the geographical location of the user may be determined. In this way, the application may retrieve geographical location information of the user base on a secure communication linkage with a device associated with the user. The device may include a mobile device with a cellular location signal, a global positioning device, a computer device, telephone device, or the like that is capable of transmitting a location of the user. In some embodiments of the invention, the application periodically or continuously requests and receives location updates from a user device associated with a user that is a part of the sharing request network in order to more accurately locate the user device and associated user and provide efficient matches based on the up-to-date location of proximate users. In other embodiments, the application initially determines the location of the user device as a home location and does not continuously track the location of the user device and instead uses the home location within the sharing request network. A user may prefer this method of location as the user may wish to opt out of continuous tracking due to privacy reasons. In some embodiments, the application requests authorization from the user before retrieving the location of the user device and associated user.

In some embodiments, the sharing request network application 150 builds the sharing request network application based on the one or more sets of user data and user profiles generated. In this way, the user profiles may be compiled within the sharing request network. These profiles may be analyzed, systematically compiled, and associated based on geographic location, interests, and/or preferences. Subsequently, a matching may occur between various user profiles requesting assets with user profiles having those assets. Furthermore, the sharing request network application may include a communication linkage with third party systems. These third party systems may include products and services that may be desired by the users on the sharing request network. These third party systems may be associated with volunteer requests, medical aid, transportation, or the like.

In some embodiments, the sharing request network application 150 generates knowledge sharing applications into the sharing request network. The knowledge database comprises a question posting and answering application generated by the users. The application may match questions posted onto the database to one or more users that have experience associated with the subject of that question. Based on the user profile, the application may identify one or more areas of expertise or experience of the user. Since the users are typically advanced aged, the user typically will have knowledge of one or more areas, such as areas of employment, building, construction, business, financial, or the like. The application may identify the experience areas of the user on the sharing request network. In some embodiments, the application identifies areas of expertise or experience of the user on the sharing request network based on information provided during generation of the user profile. As such, the application may direct questions posted onto the knowledge database to specific users with experience in that area.

In some embodiments, the sharing request network application 150 determines a match between at least two users on the sharing request system. In some embodiments, the application determines a match by comparing information and preferences contained within the user profiles of the users within the sharing request network and/or the determined geographical location of the users. In some embodiments, one or more users within the sharing request network may be matched with a third party which provides a product or service that the user requested.

In some embodiments, the application may transmit matching user information for sharing requests to one or more users. In this way, based on the user profiles, the application may match requests from one or more users to one or more users that have the resources to match the request. Furthermore, the application may reach out to third party systems, such as a doctor's office, in order to arrange doctor appointments for the two users around the same time and date.

Figure 2:
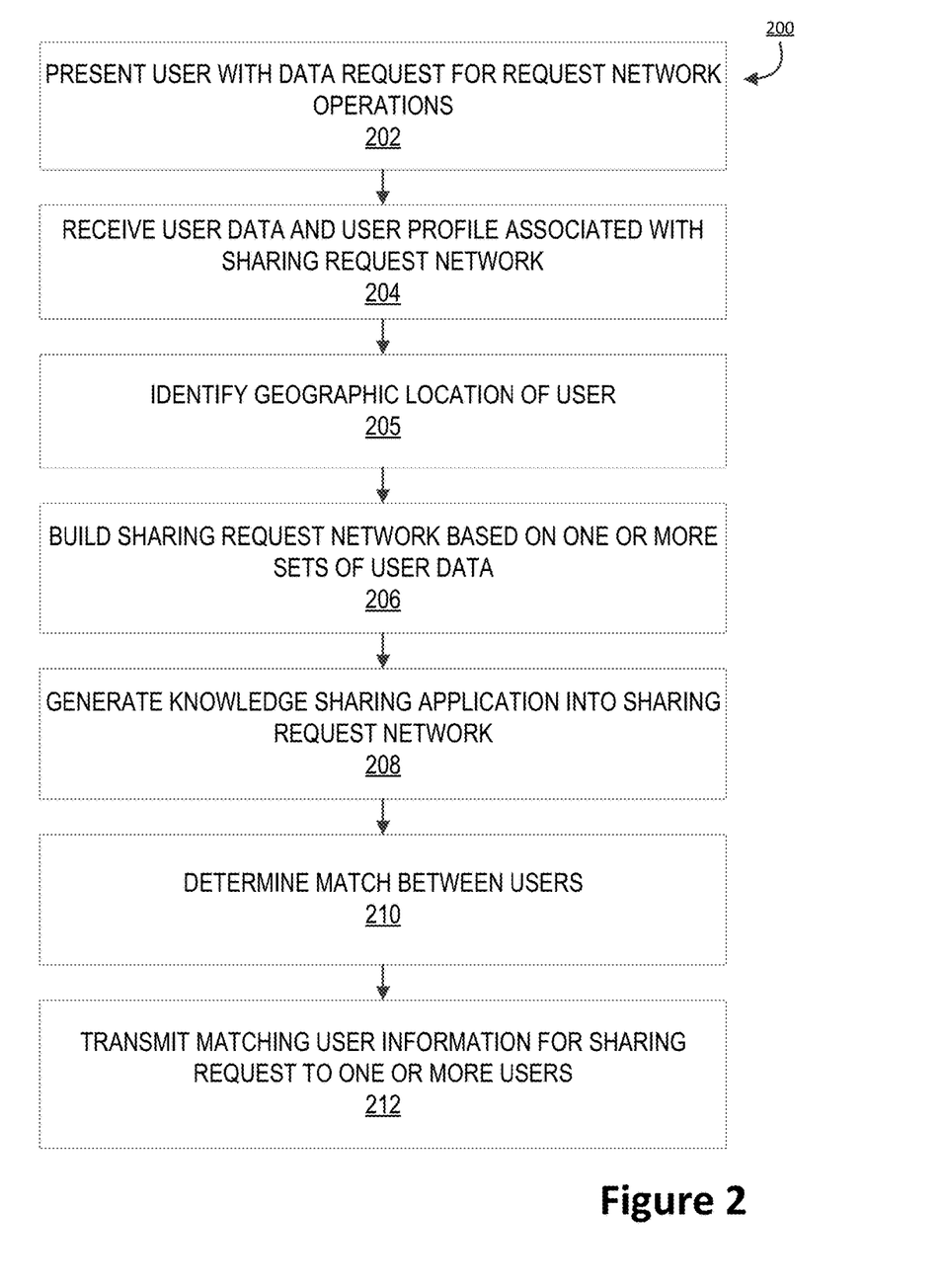
FIG. 2 provides a high level process flow illustrating generating and building a sharing request network, in accordance with one embodiment of the present invention.

FIG. 2 illustrates a high level process flow for generating and building a sharing request network 200, in accordance with one embodiment of the invention. As illustrated in block 202, the process 200 is initiated by presenting a user with data request for request network operations, for the sharing request network. As such, once a user has authenticated into the system, the system may push a request for input data for a user profile. The data request may be a request of input data to generate a user profile. The data requested may be for medical needs, social information, volunteer requests, travel requirements, and/or information in the form of questions or aids for the knowledge database.

Referring now to FIG. 4, which provides a high level process flow for generating a user profile 400, after the system presents a user with data request for request network operation in block 402, the system next prompts the user for personal information and preferences to be associated with a user profile as illustrated in block 404. In some embodiments, the system prompts the user to provide personal information such as name, address, date of birth, phone number, email, medical records, and the like. In some embodiments, personal information may include hobbies, interests, areas of expertise, and the like. In some embodiments, the system prompts the user to provide or select preferences such as preferred events that the user might personally prefer over others. For example, a user may prefer to attend a volunteer event over a social event such as a concert or other types of events. The user may rank volunteer requests higher than other requests in the preferences associated with their user profile. In some embodiments, the system prompts the user to provide or select preferences for potential user matches such as a preferred age range, sex, or the like of potential matched users. The selection of preferences may additionally allow for better matching of like-minded users with similar preferences.

In some embodiments, information collected by the system while generating the user profile such as personal information or preferred user requests as well as the user profile itself may be stored by the system in a centralized database allowing efficient searching of information in order to match users in substantially real-time. By storing the information stored within the user profile in a centralized database location, the system is able to reduce the time and memory required to perform a search of user profiles while attempting to match users.

In some embodiments, the system generates communicable linkages with one or more financial institutions associated with a user. In this way, the system may retrieve financial information associated with the user such as transaction history, financial account information, and/or the like. In some embodiments, the system uses financial information to at least partially generate a user profile, wherein the financial information may be used to provide personal information and/or user preferences. For example, a user's transaction history may show payments directed toward a particular doctor's office. The system may retrieve and store this information within the user profile of the user and use it to match the user with another user who has the same doctor and may require or possibly be able to provide transport to the doctor's office. In another example, the user's transaction history may show that the user has attended several concerts in the past. The system may identify the user's preference for attending similar events, store this information within the user profile, and match the user with other users based on this trend.

As illustrated in block 406, the system prompts a user to create a username and password to be associated with a user profile. The username and password provide identification of a user within the system while additionally providing a level of security for accessing the user profile within the application and system. In some embodiments, a user must first be authenticated by providing the username and password associated with a user profile before being allowed by the system to access the user profile and interact with other users within the sharing request network system. In some embodiments, the system automatically creates a username for a user based off of the personal information and/or preferences provided by the user in the previous step. For example, the system may create or suggest to create a username for a user that is the same as an email address associated with a user.

As illustrated in block 408, the system prompts the user to associate one or more social media accounts with the user profile. In some embodiments of the invention, the system may use information contained within the one or more social media accounts in order to populate the user profile with information related to the user. In some embodiments, the system provides social media accounts of a first user and a second user to one another upon the first user and the second user being matched.

In some embodiments, the user is prompted by the system to input data and/or personal information via the user device. Upon a user accessing the sharing request network, the system transmits a command signal to the user device causing the user device to display a graphical user interface containing fields for the user to input requested information or data.

Finally, as illustrated in block 410, the system generates a user profile associated with a user. In some embodiments of the invention, the system compiles the data and information provided by a user into a user profile. In some embodiments, the system stores the user profile in the sharing request system 140. In other embodiments, the system stores the user profile in the user device. In some embodiments, the user profile is stored within the user application on the user device.

Referring now back to FIG. 2, after the user profile has been generated, the process for generating and building a sharing request network 200 continues by receiving user data and a user profile associated with the sharing request network as illustrated in block 204. The received data is categorized and analyzed. As previously discussed, this information is utilized to generate one or more user profiles which are compiled to build the sharing request network. This network may use the profiles to match various requests of the users with other users in the same geographic area for sharing of resources. Furthermore, based on the received information, the system may determine the experience of the user for the knowledge database. The system may determine one or more social, volunteering, medical, or travel needs or aids that the user may have.

Next, as illustrated in block 205, the process 200 continues by identifying the geographic location of the user. In this way, once a user is authorized into the system, the geographical location of the user may be determined. In this way, the system may retrieve geographical location information of the user based on a secure communication linkage with a user device associated with the user. The user device may include a mobile device with a cellular location signal, a global positioning device, a computer device, telephone device, or the like that is capable of transmitting a location of the user. In some embodiments of the invention, the system periodically or continuously requests and receives location updates from a user device associated with a user that is a part of the sharing request network in order to more accurately locate the user device and associated user and provide efficient matches based on the up-to-date location of proximate users. In other embodiments, the system initially determines the location of the user device as a home location and does not continuously track the location of user device instead using the home location within the sharing request network. A user may prefer this method of location as the user may wish to opt out of continuous tracking due to privacy reasons. In some embodiments, the system requests authorization from user before retrieving the location of the user device and associated user.

As illustrated in block 206, the process 200 continues by building the sharing request network application based on the one or more sets of user data and user profiles generated. In this way, the user profiles may be compiled within the sharing request network. These profiles may be analyzed, systematically compiled, and associated based on geographic location, interests, and/or preferences. Subsequently, a matching may occur between various user profiles requesting assets with user profiles having those assets. Furthermore, the sharing request network application may include a communication linkage with third party systems. These third party systems may include products and services that may be desired by the users on the sharing request network. These third party systems may be associated with volunteer requests, medical aid, transportation, or the like. For example, a communication linkage with a third party ride sharing service or taxi service may be generated with one or more users who request transportation.

As illustrated in block 208, the process 200 continues by generating knowledge sharing applications into the sharing request network. The knowledge database comprises a question posting and answering application generated by the users. The system may match questions posted onto the database to one or more users that have experience associated with that question. Based on the user profile, the system may identify one or more areas of expertise of the user. Since the users are typically advanced aged, the user typically will have knowledge of one or more areas, such as areas of employment, building, construction, business, financial, or the like. The system may identify the experience areas of the user on the sharing request network. In some embodiments, the system identifies areas of expertise or experience of the user on the sharing request network based on information provided during generation of the user profile. As such, the system may direct questions posted onto the knowledge database to specific users with experience in that area.

In some embodiments, the knowledge database is made available to all users wherein questions may be posted public for all users of the sharing request network to view and answer. In some embodiments of the invention, skills, experience, and/or expertise of a user may be represented or displayed with a user's response to a question allowing the user who posed the question or any other users viewing the question and response to be aware of the skills, experience, and/or expertise of the user responding to the question. In some embodiments, the system may rank user responses based on the skills, experience, and/or expertise of the user responding to the question and display more qualified user responses with more prominence than less qualified responses. In other embodiments, the system may allow for a voting system wherein users within the sharing request network vote for the response that best answers the question.

As illustrated in block 210, the system determines a match between at least two users on the sharing request system. In some embodiments, the system determines a match by comparing information and preferences contained within the user profiles of the users within the sharing request network and/or the determined geographical location of the users. In some embodiments, a user within the sharing request network may be matched with a third party which provides a product or service that the user requested. In some embodiments of the invention, users and/or third parties are matched based on the determined locations of the users and/or third parties being within a predetermined distance from one another.

Finally, as illustrated in block 212, the system may transmit matching user information from sharing requests to one or more users. In this way, based on the user profiles, the system may match requests from one or more users to one or more users that have the resources to match the request. For example, the system may identify two users that receive medical aid at the same doctor's office. The system may also identify that one of the users requires transportation. The system may match these two users together such that they may travel together to an appointment. Furthermore, the system may reach out to third party systems, such as the doctor's office, in order to arrange doctor appointments for the two users around the same time and date.

In some embodiments, the system incorporates a rating system allowing for users to review past matches. In some embodiments, the rating or review is incorporated into a user's profile and made pubic to other users. In some embodiments, the system allows users to provide a ration of a past match. In some embodiments, the system allows users to provide a written review of a past match which is made public for other users to view. In some embodiments, the system allows a user to provide a recommendation and/or vouch for another user based on past experience.

In some embodiments of the invention, upon matching one or more users, the system directly transmits a notification of the match to the one or more users in addition to information associated with the matched users. In some embodiments, the system transmits a list of all matches to the user allowing the user to sort through matches by various criteria such as geographic location, information contained within user profiles, ratings, reviews, and the like. In some embodiments, the system will immediately notify the user a match via a text, automated call, email, or other form of electronic communication. In some embodiments, the system first establishes a communicable linkage between matched users allowing the users to communicate with one another before being matched.

In other embodiments of the invention, the system provides a list of initial matches and allows the user to filter the list of initial matches according to personal information, preferences, geographic location, ratings, reviews and/or the like. The user is allowed to browse the list of initial matches and select one or more final matches based on information provided to the user related to the initial matches such as. In some embodiments, the system allows the user to filter a list of initial matches for those initial matches that are known by the user on a social media account associated with the user.

In some embodiments of the invention, user profiles are public and can be viewed by users of the sharing request network. In other embodiments of the invention, user profiles and information within are private and not visible to other users. In some embodiments, a user profile is only provided or made visible to other users after a match has been determined with the other users. In other embodiments, only limited information is provided or made visible to other users after a match is made with the other users. For example, after a match is determined, a user may be provided contact information related to the matched user such as an email address, phone number, or the like. In some embodiments, the system allows a user to specify levels of privacy for information within the user profile, wherein the user may decide what information may be made public or private at certain stages of the share request process. For example, a user may want to make their skills public to all users but not release their contact information until after a match has been determined.

Figure 3:
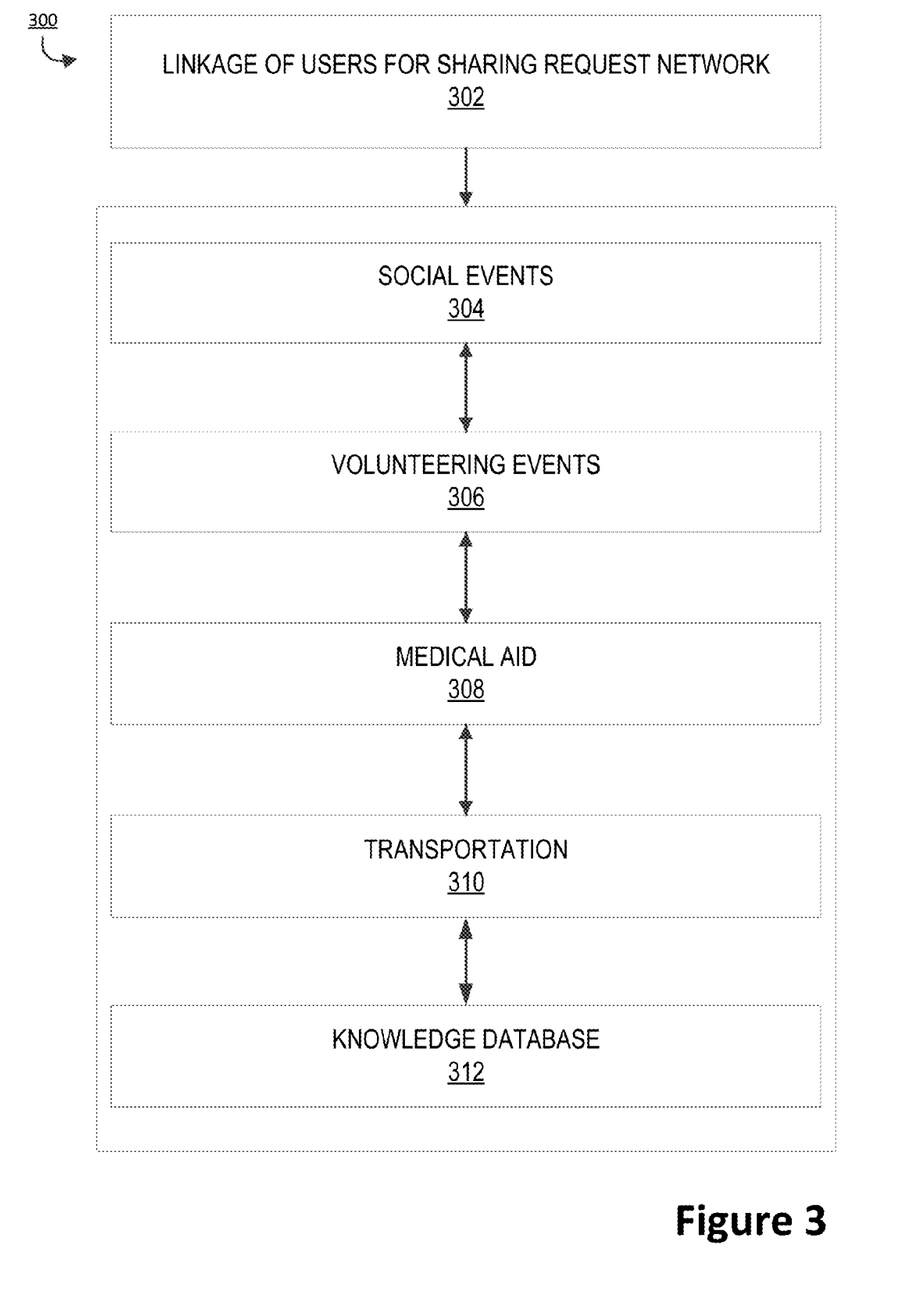
FIG. 3 provides a process map illustrating the outputs generated by the sharing request network, in accordance with one embodiment of the present invention.

FIG. 3 illustrates a process map for the outputs generated by the sharing request network 300, in accordance with one embodiment of the present invention. As illustrated in block 302, the process 300 is initiated by linking or matching users for the sharing request network. This linkage may be performed for social events 304, volunteering events 306, medical aid 308, transportation 310, and/or the knowledge database 312.

As illustrated in block 304, the sharing request network may include linkages between users for social events. In this way, the system may compare user profiles to identify geographically proximate users that have the same or similar interest in attending one or more social events 304. The social events 304 may be one or more of concerts, dinners, outings, gatherings, or the like. As such, the invention matches two or more users to a social event 304, such that the users may attend the event together, arrange transportation for the event, or the like. For example, a first user may wish to attend a concert, but does not wish to attend alone and does not know anyone else who would go. The system may identify a second user with the same desire to attend the concert and match the first and second users allowing them to communicate and plan for attendance of the concert together.

Furthermore, the system may communicate with the third party system that organized the social event 304 in order to purchase tickets for the event if necessary. The system may allow communication between the users and the third party system for coordination and participation in the event.

In another embodiment, social events 304 may also include shopping, such as at grocery stores, clothing stores, and the like. In this way, users may be able to pick up products or services for the other users to aid the other users in their shopping needs. For example, a first user may have difficulty navigating a grocery store due to an injury, old age, or the like. The system may identify a second user who is planning on shopping at a grocery store location and match the second user with the needs of the first user. Upon matching, the first and second users may communicate and arrange for the second user to shop for groceries at the grocery store on behalf of the first user.

In yet another embodiment, social events 304 may also include travel. A user may wish to travel to a location for leisure with a companion. In this way, the system may match users with the desire to travel to the same location. In some embodiments, the system may additionally match the users with a third party such as a travel agency, one or more hotels at the desired location, and/or the like to assist the matched users to coordinate the details of the travel.

As illustrated in block 306, the sharing request network may include linkages between users for volunteering events. In this way, the system may find one or more volunteer opportunities for advanced age individuals. In this way, the system may reach out and generate a communication linkage with third party systems associated with volunteer organizations and volunteer opportunities. Furthermore, the system may match a user to a volunteer event that he/she may be interested in based on the user profile. The system may match the user with other users with a similar interest. Additionally, the system may allow communication between the users and the third party system for coordination and participation in the event.

As illustrated in block 308, the sharing request network may include linkages between users for medical treatments. In this way, the system may identify, based on the user profile, one or more medical aid providers that the user uses for medical treatment. The system may match the user with other users that use the same medical aid provider. In this way, users may be able to arrange transportation together for appointments, attend appointments together, aid in travel and transportation to the medical provider and the like. The system may communicate with the users and third party system associated with the medical provider in order to arrange appointment times at the same time, coordinate transportation, and the like.

As illustrated in block 310, the sharing request network may include linkages between users for transportation. In some instances, users may not have a means of transportation or an ability for transportation. As such, the system may link two or more users together for transportation to an event that each of the users is attending. In this way, the system may determine from the user profile one or more users that have means for traveling, such as vehicles, public transportation, or the like. Then, the system may determine two or more users that are attending the same event. The system may then link the two or more users together for coordinating transportation. The system may allow communication between the users and a third party system for coordination and participation in the event. In some embodiments, the system may identify that the matched users may require transportation to and/or from the event and allow for communication between the users and a third party system related to transportation such as a ride sharing service, taxi service, shuttle service, or the like.

Finally, as illustrated in block 312, the sharing request network may include linkages between users for the knowledge database. Typically, aging individuals have professional or personal experiences, the user may be able to provide advice via the system and the system may generate rewards based on knowledge or advice provided. Since the users are typically advanced aged, the user typically will have knowledge of one or more areas, such as areas of employment, building, construction, business, financial, or the like. The system may identify the experience areas of the user on the sharing request network. As such, the system may direct questions posted onto the knowledge database to specific users with experience in that area. In some embodiments of the invention, the reward generated by the system is a monetary reward such as gift card, discount, coupon, or the like. In some embodiments, the reward generated by the system is a nonmonetary reward such as points, a badge, or other nonmonetary forms of recognition within the application.

In some embodiments, a user may receive a reward from another user for answering a question on the knowledge database within the sharing request network. In some embodiments, the reward may be related to a request of the user who answered the questions. In some embodiments, the knowledge database allows users to barter or exchange knowledge, expertise, and/or other user resources as rewards within the knowledge database. For example, a first user may be knowledgeable on the subject of plumbing and have a question related to his or her accounts, whereas a second user may be a retired accountant who has an issue with the plumbing of his or her house. The first user may offer to lend his or her expertise in plumbing to fix the issue at the second user's house in return for receiving accounting advice from the second user.

In some embodiments of the invention one or more of the systems described herein may be combined with each other, or otherwise perform the functions of the other systems described herein. In other embodiments of the invention one or more of the applications described herein may be combined with each other, or otherwise perform the functions of the other applications described herein. Furthermore, the applications may be any type of application, such as an application stored on a desktop, server, or other device, a mobile application stored on a mobile device, a cloud application, or other like application. As such, the applications described herein, or portions of the applications described herein may be stored and operated on any of the systems or devices described herein. For example, a portion of one or more applications may be stored on the user device, or may be included as a portion of financial institution applications, such as an online banking application, in order to achieve embodiments of the inventions described herein.

It should be understood, that the systems and devices described in FIG. 1, or other devices not specifically described herein, may be configured to establish a communication link with each other in order to accomplish the steps of the processes described herein. The link may be an internal link within the same entity (e.g., within the same financial institution or device provider) or a link with the other systems of entities (e.g., social networking systems, third-party systems, or the like). In some embodiments, the systems may be configured for monitoring the applications and devices that the system(s) utilize as data sources. The information received from monitoring may be provided via wireless network path portions through the Internet. When the systems or devices are not monitoring a source or are not being monitoring, the information need not be transmitted from the source through the Internet to the destination, although it could be. The sources of information may be made continuously available, however, continuously available does not necessarily mean that the sources actually continuously generates data, but that a source is continuously available to generate and send data real-time (e.g., instantaneously and/or within a few seconds, or the like) of receiving a request for it. In any case, the sources may be continuously available to receive and/or generate information, in some cases in digitized data in Internet Protocol (IP) packet format. In response to continuously monitoring the real-time data feeds from the various systems or devices, the system may be configured to provide target information to the user and/or allow the user to make changes to or control the applications and/or devices.

Moreover, it should be understood that the process flows described herein include transforming the information sent and/or received from the applications of the different systems (e.g., internally or externally) and/or the devices from one or more data formats into a data format associated with an application for display to the user on the user device. There are many ways in which information is converted within the system environment. This may be seamless, as in the case of upgrading to a newer version of a computer program. Alternatively, the conversion may require processing by the use of a special conversion program, or it may involve a complex process of going through intermediary stages, or involving complex "exporting" and "importing" procedures, which may converting to and from a tab-delimited or comma-separated text file. In some cases, a program may recognize several data file formats at the data input stage and then is also capable of storing the output data in a number of different formats. Such a program may be used to convert a file format. If the source format or target format is not recognized, then at times a third program may be available which permits the conversion to an intermediate format, which can then be reformatted.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s).

The computer-executable program code may also be loaded onto a computer or other programmable data processing apparatus to cause a series of operational steps to be performed on the computer or other programmable apparatus to produce a computer-implemented process such that the code portions which execute on the computer or other programmable apparatus provide steps for implementing the functions/acts specified in the flowchart and/or block diagram block(s). Alternatively, computer program implemented steps or acts may be combined with operator or human implemented steps or acts in order to carry out an embodiment of the invention.

Embodiments of the present invention are described above with reference to flowcharts and/or block diagrams. It will be understood that steps of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

INCORPORATION BY REFERENCE

To supplement the present disclosure, this application further incorporates entirely by reference the following commonly assigned patent applications:

| U.S. patent application Ser. No. | Title | Filed On |
|---|---|---|
| 15/223,469 | SYSTEM FOR TRIGGERING OF LIVING OPTION RESOURCE ALLOCATION | Concurrently herewith |
| 15/223,458 | GEOGRAPHIC SELECTION SYSTEM BASED ON RESOURCE ALLOCATION AND DISTRIBUTION | Concurrently herewith |
| 15/223,558 | WEARABLE DEVICE FOR REAL-TIME MONITORING OF PARAMETERS AND TRIGGERING ACTIONS | Concurrently herewith |
| 15/223,880 | SYSTEM ENVIRONMENT FOR USER-SPECIFIC PROGRAM | Concurrently herewith |

| U.S. patent application Ser. No. | Title | Filed On |
|---|---|---|
| | AGGREGATION AND NON-COLLOCATED THIRD PARTY SYSTEM EXTRACTION AND DEPLOYMENT | |

What is claimed is:

1. A system for building a sharing request network, the system comprising:
 a memory device with computer-readable program code stored thereon;
 a communication device;
 a processing device operatively coupled to the memory device and the communication device, wherein the processing device is configured to execute the computer-readable program code to:
  receive authentication and acceptance from a user for entry into the sharing request network;
  generate a communication link with a user device for extraction of positioning data associated with the user device, wherein the user device is associated with the user;
  generate a user profile, stored in a centralized database, identifying user request events and a location of the user device from the positioning data;
  based on the user profile, match the user to one or more additional users and third party systems for event coordination, wherein the third party systems offer products or services; and
  trigger a communicable linkage between the user, the one or more additional users, and the third party systems for coordination of resource sharing and knowledge sharing, wherein matching user information is transmitted and presented to matched users over the communicable linkage, wherein knowledge sharing further comprises:
   generating a knowledge sharing database application;
   receiving and storing one or more questions from users of the sharing request network in the knowledge sharing database application;
   directing the one or more questions to a responding user based on personal or professional skills, experience, or expertise of the responding user; and
   generating a reward for a responding user based on the responding user answering the one or more questions.

2. The system of claim 1, wherein generating the user profile further comprises:
 transmitting a control signal to the user device causing the user device to display a data request via a graphical user interface;
 prompting the user for personal information and user preferences;
 generating a username and password associated with the user profile;
 linking one or more social media accounts associated with the user to the user profile; and
 extracting information from the personal information, the user preferences, and the one or more social media accounts to generate the user profile.

3. The system of claim 2, wherein prompting the user for personal information and user preferences further comprises:
 requesting access to one or more financial accounts associated with the user; and
 extracting personal information, financial account information, and transaction history from the one or more financial accounts to be used for at least partially generating the user profile.

4. The system of claim 1, wherein matching the user to one or more additional users and third party systems further comprises:
 determining the location of the user device based on extracted positioning data;
 determining one or more additional locations of one or more additional user devices associated with the one or more additional users based on additional positioning data extracted from the one or more additional user devices; and
 based on determining that the first location and the one or more additional locations are within a predetermined distance of each other, triggering a match between the user, the one or more additional users, and the third party systems.

5. The system of claim 1, wherein the third party systems for event coordination comprise systems for transportation coordination and sharing, wherein the positioning data associated with the user device is transmitted to the third party systems for determining the location of the user and coordinating transportation.

6. A computer program product for building a sharing request network, the computer program product comprising at least one non-transitory computer readable medium having computer-readable program code portions embodied therein, the computer-readable program code portions comprising:
 an executable portion configured for receiving authentication and acceptance from a user for entry into the sharing request network;
 an executable portion configured for generating a communication link with a user device for extraction of positioning data associated with the user device, wherein the user device is associated with the user;
 an executable portion configured for generating a user profile, stored in a centralized database, identifying user request events and a location of the user device from the positioning data;
 an executable portion configured for matching, based on the user profile, the user to one or more additional users and third party systems for event coordination, wherein the third party systems offer products or services; and
 an executable portion configured for triggering a communicable linkage between the user, the one or more additional users, and the third party systems for coordination of resource sharing and knowledge sharing, wherein matching user information is transmitted and presented to matched users over the communicable linkage, wherein knowledge sharing further comprises:
  generating a knowledge sharing database application;
  receiving and storing one or more questions from users of the sharing request network in the knowledge sharing database application;
  directing the one or more questions to a responding user based on personal or professional skills, experience, or expertise of the responding user; and generating a reward for a responding user based on the responding user answering the one or more questions.

7. The computer program product of claim 6, wherein generating the user profile further comprises:
transmitting a control signal to the user device causing the user device to display a data request via a graphical user interface;
prompting the user for personal information and user preferences;
generating a username and password associated with the user profile;
linking one or more social media accounts associated with the user to the user profile; and
extracting information from the personal information, the user preferences, and the one or more social media accounts to generate the user profile.

8. The computer program product of claim 7, wherein prompting the user for personal information and user preferences further comprises:
requesting access to one or more financial accounts associated with the user; and
extracting personal information, financial account information, and transaction history from the one or more financial accounts to be used for at least partially generating the user profile.

9. The computer program product of claim 6, wherein matching the user to one or more additional users and third party systems further comprises:
determining the location of the user device based on extracted positioning data;
determining one or more additional locations of one or more additional user devices associated with the one or more additional users based on additional positioning data extracted from the one or more additional user devices; and
based on determining that the first location and the one or more additional locations are within a predetermined distance of each other, trigger a match between the user, the one or more additional users, and the third party systems.

10. The computer program product of claim 6, wherein the third party systems for event coordination comprise systems for transportation coordination and sharing, wherein the positioning data associated with the user device is transmitted to the third party systems for determining the location of the user and coordinating transportation.

11. A computer-implemented method for building a sharing request network, the method comprising:
receiving authentication and acceptance from a user for entry into the sharing request network;
generating a communication link with a user device for extraction of positioning data associated with the user device, wherein the user device is associated with the user;
generating a user profile, stored in a centralized database, identifying user request events and a location of the user device from the positioning data;
matching, based on the user profile, the user to one or more additional users and third party systems for event coordination, wherein the third party systems offer products or services; and
triggering a communicable linkage between the user, the one or more additional users, and the third party systems for coordination of resource sharing, wherein matching user information is transmitted and presented to matched users over the communicable linkage, wherein knowledge sharing further comprises:
generating a knowledge sharing database application;
receiving and storing one or more questions from users of the sharing request network in the knowledge sharing database application;
directing the one or more questions to a responding user based on personal or professional skills, experience, or expertise of the responding user; and
generating a reward for a responding user based on the responding user answering the one or more questions.

12. The computer-implemented method of claim 11, wherein generating the user profile further comprises:
transmitting a control signal to the user device causing the user device to display a data request via a graphical user interface;
prompting the user for personal information and user preferences;
generating a username and password associated with the user profile;
linking one or more social media accounts associated with the user to the user profile; and
extracting information from the personal information, the user preferences, and the one or more social media accounts to generate the user profile.

13. The computer-implemented method of claim 12, wherein prompting the user for personal information and user preferences further comprises:
requesting access to one or more financial accounts associated with the user; and
extracting personal information, financial account information, and transaction history from the one or more financial accounts to be used for at least partially generating the user profile.

14. The computer-implemented method of claim 11, wherein matching the user to one or more additional users and third party systems further comprises:
determining the location of the user device based on extracted positioning data;
determining one or more additional locations of one or more additional user devices associated with the one or more additional users based on additional positioning data extracted from the one or more additional user devices; and
based on determining that the first location and the one or more additional locations are within a predetermined distance of each other, trigger a match between the user, the one or more additional users, and the third party systems.

15. The computer-implemented method of claim 11, wherein the third party systems for event coordination comprise systems for transportation coordination and sharing, wherein the positioning data associated with the user device is transmitted to the third party systems for determining the location of the user and coordinating transportation.

16. The computer-implemented method of claim 11, wherein the user profile is stored in a centralized database.

* * * * *